United States Patent [19]

Vassilev et al.

[11] 4,184,363

[45] Jan. 22, 1980

[54] METHOD OF AND APPARATUS FOR MEASURING THE THICKNESS OF ONE LIQUID OVERLYING ANOTHER

[75] Inventors: Grigor D. Vassilev; Zdravko A. Yordanov; Lyubomir A. Stoyanov; Rali V. Ralev; Kosta M. Kostov, all of Varna, Bulgaria

[73] Assignee: So "Voden Transport", Varna, Bulgaria

[21] Appl. No.: 905,548

[22] Filed: May 12, 1978

[51] Int. Cl.² .................... G01N 33/18; G01N 33/28
[52] U.S. Cl. ................................................. 73/61.1 R
[58] Field of Search ............................. 73/53, 61.1 R

[56] References Cited

U.S. PATENT DOCUMENTS

| | | | |
|---|---|---|---|
| 3,222,928 | 12/1965 | Walker | 73/53 X |
| 3,481,182 | 12/1969 | Lineberg | 73/61.1 R |
| 3,511,083 | 5/1970 | Reay et al. | 73/61.1 R |
| 3,626,751 | 12/1971 | Overbeck et al. | 73/61.1 R |

FOREIGN PATENT DOCUMENTS 261948 5/1968 Austria .................................. 73/61.1 R

*Primary Examiner*—Gerald Goldberg
*Assistant Examiner*—Joseph W. Roskos
*Attorney, Agent, or Firm*—Karl F. Ross

[57] ABSTRACT

A method of and an apparatus for measuring the thickness of one liquid layer, e.g. oil, overlying another liquid in which a conical body is lowered into the liquids until the upper layer surface reaches the neck of the cone and a sensor detects the interface, whereupon thickness is determined as a function of the height of the overlying layer in the cone.

4 Claims, 1 Drawing Figure

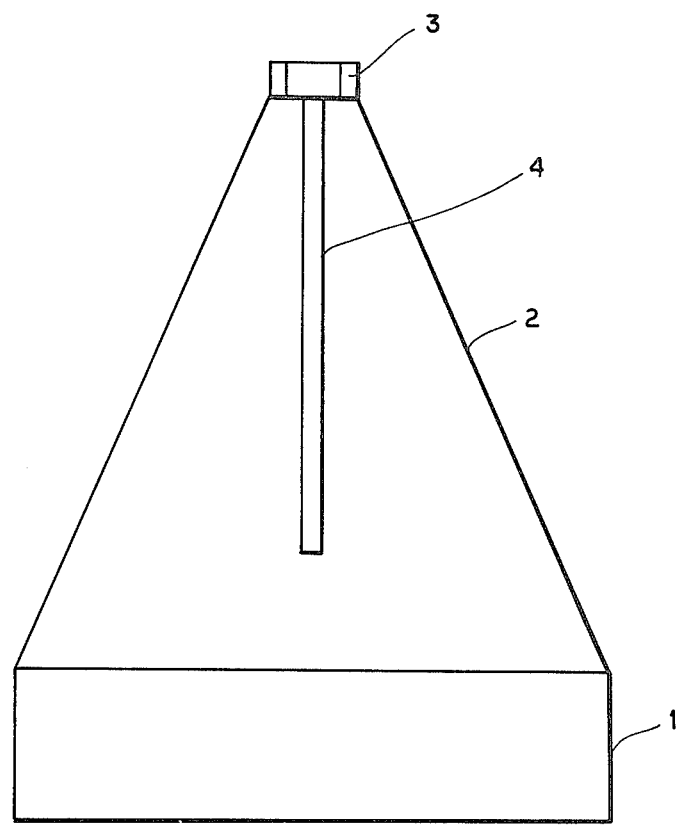

METHOD OF AND APPARATUS FOR MEASURING THE THICKNESS OF ONE LIQUID OVERLYING ANOTHER

FIELD OF THE INVENTION

The present invention relates to a method of and to an apparatus for measuring the thickness of a layer of one liquid overlying another and, more particularly, for the quantitative determination of the amount of petroleum derivatives overlying the water, e.g. in the case in which an accidental spill of petroleum products on water has occurred and it is desired to ascertain the danger of explosion or pollution of territorial waters from a ship.

BACKGROUND OF THE INVENTION

It is known to measure the thickness of a petroleum layer over th surface of water by visually ascertaining the thickness because of different colors on the water surface.

A disadvatage of this method is that it depends upon subjective color sense and adatation to the light background by the operator as awell as to meteorological circumstances during the measurement. Layer thicknesses over more than two microns cannot be effectively measured because mistakes occur to a high degree.

OBJECTS OF THE INVENTION

These objects are attained, in accordance with the present invention, by the use of a downwardly open, upwardly tapered hollow body provided with a sensor which detects the free surface of the upper liquid and the interface between the two liquids when the hollow body is lowered with its broad-base downwardly, into the liquid.

Because of the upward taper of the hollow body, the distance between the two sensed points is considerably greater than the thickness of the liquid on the surface, although it is related thereto by the geometry of the device so that the distance measurement is readily translated to the actual thickness of the upper layer in the body of the lower layer.

According to the apparatus aspects of the invention, the broad base of the tapered body is formed with an apron whose generatrix is parallel to the axis of the device and the sensor is mounted at the upper narrow end of the tapered body. A second sensor can detect the location of the interface and can extend downwardly from the neck.

The device has the advantage of measuring a relatively thick body of the upper liquid, in spite of the comparative thinness of the layer thereof on the body of the second liquid, and that the measurement takes place over a well defined area, rather than at a single point. The results are independent of the nature of the liquids and the measurement precision is many times greater than that otherwise obtainable.

BRIEF DESCRIPTION OF THE DRAWING

The sole FIGURE of the drawing is an elevational view of an apparatus for carrying out the method of the present invention.

SPECIFIC DESCRIPTION

The apparatus shown in the drawing comprises a a lower enveloping part or apron 1 extending parallel to the axis of the device and formed at the broad base of a reductor or upwardly converging frustoconical or frustopyramidal hollow body 2 at the narrow base or top (neck) of which is a sensor 3 for detecting the free surface of the upper liquid. Another sensor 4 extends downwardly from the neck to detect the lication of the interface, i.e. the dividing line between the two fluids.

In operation, the device, as shown is lowered into the body of liquid which may be water overlain by a layer of oil until the upper surface of the oil layer reaches the sensor 3. The sensor 4 detects the location of the interface and the distance between the interface and the free surface are ascertained and translated, based upon the geometry of the device into a thickness of the oil on the water into which the device has been introduced. Where the tapered portion 2 is a frustocone, the apron 1 is a cylinder and where the tapered portion 2 is frustopyramid, the aron is a parallelepiped.

The inner srface of the apron 1 and the tapered portion 2 can be coated with an oleophobic substance.

We claim:

1. A method of determining the thickness of a first liquid overlying a second liquid in a body of the second liquid, said method comprising the steps of:

lowering an upwardly converging tapered hollow body having a downwardly extending apron at the broad base of the hollow body, into the liquids whereby said apron defines an area at which the measurement is to be taken, until the upper surface of said first liquid reaches the upper end of said body;

sensing the presence of the upper surface of the first liquid when it reaches said upper end;

sensing the location of the interface between said liquids upon the detection of the upper surface of the first liquid reaching said upper end, thereby ascertaining the height of the first liquid in said hollow body; and converting said height to a measure of the original thickness of the first liquid on the second liquid over said area.

2. An apparatus for measuring the thickness of a first liquid on a second liquid in a body of said second liquid, said apparatus comprising:

an upwardly converging tapered hollow body formed with a downwardly turned broad base and an upwardly open narrow neck;

an apron extending downwardly from said body around said broad base and adapted to enter said body of said second liquid to define an area therein in which a measurement is to be taken upon lowering of said hollow body at said neck for detecting the rise of the upper surface of said first liquid to said neck in said hollow body upon such lowering; and a second sensor extending downwardly along said hollow body for ascertaining the location of the interface between said liquids when said surface reaches said neck, thereby providing a measurement of the height of the first liquid in said hollow body and enabling the evaluation of the height in terms of the actual thickness of the first liquid layer on said body of said second liquid over the region encompassed by said apron.

3. The apparatus defined in claim 2 wherein said hollow body is a frustocone, said apron is cylindrical and the interior of said hollow body and said apron is coated with an oleophobic substance.

4. The apparatus defined in claim 2 wherein said hollow body is frustopyramidal, said apron is parallelepiped and the interior of said apron and sai.. hollow body are coated with an oleophobic substance.

* * * * *